United States Patent [19]

Wick

[11] 4,344,873

[45] Aug. 17, 1982

[54] POTTING MEDIUM FROM POLYURETHANES

[75] Inventor: Gerhard Wick, Obernburg, Fed. Rep. of Germany

[73] Assignee: Akzo NV, Arnhem, Netherlands

[21] Appl. No.: 243,342

[22] Filed: Mar. 13, 1981

[30] Foreign Application Priority Data

Mar. 15, 1980 [DE] Fed. Rep. of Germany ....... 3010030

[51] Int. Cl.$^3$ .................... C08L 91/00; C08G 18/24; C08G 18/75; C08G 18/77
[52] U.S. Cl. ....................................... 528/58; 528/73; 528/77; 210/321.2; 528/74.5; 528/60; 523/112
[58] Field of Search ............... 260/18 TN; 528/67, 58

[56] References Cited

U.S. PATENT DOCUMENTS

| | | | |
|---|---|---|---|
| 2,983,693 | 5/1961 | Sievers | 260/18 TN |
| 3,047,520 | 7/1962 | Fiel | 260/18 TN |
| 3,274,134 | 9/1966 | Ramos | 260/18 TN |
| 3,483,150 | 12/1969 | Ehrlich et al. | 260/18 |
| 3,546,148 | 12/1970 | Diamond et al. | 260/18 |
| 3,691,117 | 9/1972 | Messerly | 260/18 TN |
| 3,965,073 | 6/1976 | Olstowski et al. | 528/58 |
| 4,038,239 | 7/1977 | Coyner et al. | 260/33.6 |
| 4,038,304 | 7/1977 | Kazama et al. | 528/58 |
| 4,045,527 | 8/1977 | Babayan et al. | 528/58 |

FOREIGN PATENT DOCUMENTS

| | | |
|---|---|---|
| 1204100 | 9/1970 | United Kingdom . |
| 1389219 | 4/1975 | United Kingdom . |
| 1539266 | 1/1979 | United Kingdom . |
| 1542392 | 3/1979 | United Kingdom . |
| 2021130 | 11/1979 | United Kingdom . |

*Primary Examiner*—H. S. Cockeram
*Attorney, Agent, or Firm*—Michael J. Striker

[57] ABSTRACT

Potting media based on polyurethanes produced with castor oil, a process for their preparation as well as their use. To at least one of the ingredients of the potting medium is added a dialkyltin compound in an amount resulting in a content of from about 5 to 50 ppm, calculated as elementary tin, of the dialkyltin compound. A diisocyanate based on a carbon ring compound in stoichiometric excess is reacted with a mixture of castor oil and trimethylolpropane to a prepolymer having NCO-groups. Then the prepolymer is mixed with castor oil or a mixture of castor oil and trimethylolpropane for crosslinking. Preferred diisocyanates are aromatic diisocyanates having up to about 30 carbon atoms.

The potting media exhibit a favorable course of the viscosity, wet excellently and distribute very rapidly and are particularly suited for the embedding of membranes.

39 Claims, No Drawings

POTTING MEDIUM FROM POLYURETHANES

DESCRIPTION

BACKGROUND OF THE INVENTION

1. Field of the Invention

The present invention relates to potting materials and media based on polyurethanes produced with castor oil, to a process for their preparation as well as to their use.

2. Brief Description of the Background of the Invention Including Prior Art

Potting relates to a process in which a material, or an assembly of small discrete units, is coated with, or imbedded in, a molten film, sheath or foam usually of an elastomer such as a polyurethane. A foam forming plastic such as polyurethane may be used to fill the spaces between various components so that they are imbedded in and supported by the foam. Plastics such as polyurethanes used for this purpose are often called potting compounds.

In microencapsulation a material is enclosed in capsules ranging from 20 to 150 micrometers in diameter, which are composed of polymeric substances such as polyurethanes.

A polyurethane is a thermoplastic polymer, which can be made polysetting, produced by the condensation reaction of a polyisocyanate and a hydroxyl containing material for example a polyol derived from propyleneoxide. The basic polymer unit is formed as follows: $R_1NCO + R_2OH \rightarrow R_1NHCOOR_2$. Polyurethane elastomers show good resistance to abrasion, weathering and organic solvents, they tend to harden and to become brittle at low temperatures and they are combustible.

SUMMARY OF THE INVENTION

1. Purposes of the Invention

It is an object of the present invention to provide improved compositions for potting media based on polyurethanes and a suitable catalyst.

It is another object of the present invention to provide an improved, more economic and easier to handle method for the production of potting compounds.

It is a further object of the present invention to provide embedding media suitable for artificial organs and for the embedding of membranes into artificial organs as well as for delicate embedding tasks.

These and other objects of the present invention will become evident from the description which follows.

2. Brief Description of the Invention

The present invention provides a potting medium derived from castor oil, trimethylolpropane and a diisocyanate based on a carbon ring compound and on a dialkyltin compound in an amount of from about 5 to 50 and preferably 5 to 15 parts per million calculated for elementary tin.

The carbon ring compound can comprise up to about 30 carbon atoms and preferably up to about 15 carbon atoms. The diisocyanate based on a carbon ring compound can comprise an aromatic diisocyanate such as for example 4,4'-diphenylmethane-diisocyanate. The diisocyanate based on a carbon ring compound can comprise an alicyclic diisocyanate such as for example 3-isocyanatomethyl-3,5,5-trimethylol-cyclohexyl-isocyanate. Preferably the percentage of 3-isocyanatomethyl-3,5,5-trimethylol-cycylohexyl-isocyanate relative to the total amount of diisocyanate based on a carbon ring compound is from about 10 to 50 mole percent. The 3-isocyanatomethyl-3,5,5-trimethylol-cyclohexyl-isocyanate can have a content of from about 18 to 28 mole percent of dimeric or trimeric diisocyanate.

The polymer can include groups derived from a prepolymer having NCO-groups and containing groups derived from trimethylolpropane, castor oil and a diisocyanate based on a carbon ring compound. The polymer can include groups derived from the prepolymer reacted with castor oil or from the prepolymer reacted with a mixture of castor oil and trimethylolpropane.

The dialkyltin compound can comprise up to about 50 carbon atoms and preferably up to about 30 carbon atoms. The dialkyltin compound can comprise dialkyltin-dialkanoates such as for example dibutyltin-dilaurate and di-n-butyltindinonanoate, and dialkyltin-mercaptides.

There is also provided a method for production of a potting medium which comprises adding to at least one of the ingredients employed a dialkyltin compound in an amount resulting in a content of the potting medium of from about 5 to 50 ppm calculated for elementary tin and preferably from about 5 to 15 ppm, reacting a diisocyanate based on a carbon ring compound in stochiometric excess with a mixture of castor oil and trimethylolpropane to a prepolymer having NCO-groups; and mixing the prepolymer with castor oil for crosslinking.

In addition, trimethylolpropane can be added to the castor oil employed in mixing with the prepolymer. The potting medium can be hardened. Dialkyl tin can be added to the prepolymer composition or to the castor oil to be mixed with the prepolymer. The prepolymer can be prepared at a temperature from about 40° to 100° C. and preferably from about 60° to 75° C. The carbon ring compound can comprise up to about 30 carbon atoms and preferably up to about 15 carbon atoms. The diisocyanate based on a carbon ring compound can comprise an aromatic diisocyanate such as for example 4,4'-diphenylmethane-diisocyanate or an alicyclic diisocyanate such as for example 3-isocyanatomethyl-3,5,5-trimethylol-cyclohexyl-isocyanate.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying examples.

DESCRIPTION OF INVENTION AND PREFERRED EMBODIMENTS

In accordance with the present invention there is provided a potting medium on the basis of castor oil and polyurethanes which comprises 5 to 50 ppm, calculated as elementary tin, of a dialkyltin compound. The polyurethane can be prepared by reaction of an aromatic diisocyanate with a mixture of castor oil and trimethylolpropane to a prepolymer having NCO-groups followed by crosslinking of the prepolymer with castor oil or a mixture of castor oil and trimethylolpropane. The polyurethane can also be prepared by reacting an aromatic diisocyanate with a mixture of castor oil and trimethylolpropane to a prepolymer comprising NCO-groups followed by crosslinking of the prepolymer with castor oil or a mixture of castor oil and trimethylolpropane, wherein 4,4'-diphenylmethane-diisocyanate having a contents of from about 18 to 28 mole percent of dimerized or trimerized diisocyanate is employed as the aromatic diisocyanate. The polyurethane can also be prepared by reaction of an aromatic diisocyanate with a mixture of castor oil and trimethylolpropane to a prepolymer comprising NCO-groups and cross-linking of the prepolymer with castor oil or a mixture of castor oil and trimethylolpropane, wherein an aromatic diisocyanate is employed comprising from about 10 to 50 mole percent of 3-isocyanatomethyl-3,5,5-trimethylolcyclohexyl-isocyanate.

Further, in accordance with the invention there is provided a method for production of a potting medium from polyurethanes, wherein as a catalyst a dialkyltin compound in amounts of from about 5 to 50 ppm calculated as elementary tin is employed. An aromatic isocyanate in stochiometric excess is reacted with a mixture of castor oil and trimethylolpropane to a prepolymer comprising NCO-groups, the prepolymer is mixed with castor oil or a mixture of castor oil and trimethylolpropane for crosslinking and after the embedding the mixture is hardened. An aromatic diisocyanate in stochiometric excess can also be reacted with a mixture of castor oil and trimethylolpropane to a prepolymer having NCO-groups, the prepolymer is mixed with castor oil or a mixture of castor oil and trimethylolpropane for crosslinking and the mixture is hardened after the embedding, wherein 4,4'-diphenylmethane-diisocyanate is employed as the aromatic diisocyanate. An aromatic diisocyanate in stochiometric excess can also be reacted with a mixture of castor oil and trimethylolpropane to a prepolymer comprising NCO-groups, the prepolymer can be mixed with castor oil or a mixture of castor oil and trimethylolpropane for crosslinking and the mixture can be hardened after the embedding, wherein the aromatic diisocyanate employed can comprise from about 10 to 50 mole percent 3-isocyanatomethyl-3,5,5-trimethylol-cyclohexyl-isocyanate.

In German Pat. No. 2,813,197 there are disclosed potting media based on polyurethanes prepared with castor oil, a method for their production as well as their use. The polyurethanes in accordance with this patent are obtained by reacting an aromatic diisocyanate with a mixture of castor oil and trimethylolpropane to a prepolymer comprising NCO-groups and crosslinking the prepolymer with castor oil or a mixture of castor oil and trimethylolpropane. The potting media disclosed in this patent disclosure are characterized by excellent properties such as high hardness, clearness, compatibility with blood and good processing properties. They are particularly suitable for embedding of membranes such as hollow threads, hollow fibers, tube foils, films; these can be employed for the construction of dialysers and in particular hemodialysers.

In German patent disclosure No. 2,855,243 are disclosed potting media of polyurethanes based on castor oil, methods for their production as well as their use, where 4,4'-diphenylmethane-diisocyanate is employed as the aromatic diisocyanate having a contents of from about 18 to 28 mole percent of dimerized or trimerized diisocyanate. The products mentioned in German patent disclosure No. 2,855,243 are distinguished for example by good stability during storage and good viscosity properties.

In German patent disclosure No. 2,907,501 there are disclosed potting media of polyurethanes based on castor oil, methods for their production as well as their use, where an aromatic diisocyanate is employed comprising from about 10 to 50 mole percent 3-isocyanatomethyl-3,5,5-trimethylolcyclohexyl-isocyanate. The polyurethane embedding media disclosed in German patent disclosure No. 2,907,501 are characterized in particular by improved adhesive properties. The present invention provides additional improvements and improved production, which is more economic and better to be handled.

An aromatic diisocyanate such as for example 4,4'-diphenylmethane-diisocyanate having a contents of from about 18 to 28 mole percent of dimerized and trimerized diisocyanate or as for example including from about 10 to 50 mole percent of 3-isocyanatomethyl-3,5,5-trimethylol-cyclohexyl-diisocyanate, employed in stochiometric excess is reacted with a mixture of castor oil and trimethylolpropane to a prepolymer having NCO-groups. The prepolymer is mixed with castor oil or a mixture of castor oil and trimethylolpropane for crosslinking and after the embedding the mixture is hardened. To one of the starting materials were added from about 5 to 50 ppm, calculated as elementary tin based on the embedding medium, of a dialkyltin compound. A preferred amount of dialkyltin compound is from about 5 to 15 ppm. Preferred dialkyltin compounds include dialkyltin-alkanoates such as for example dibutyltindilaurate or di-n-butyltindinonanoate. Also useful as dialkyltin compounds are dialkyltin-mercaptides. A preferred tin compound is the product METATIN catalyst 713 distributed by Acima AG fuer chemische Industrie Buchs SG, Switzerland during 1980.

The potting media in accordance with the present invention are particularly suitable for the embedding of membranes and in particular for membranes in artificial organs. The membranes to be embedded are preferably provided as hollow fibers, hollow threads, tube foils, films or flat foils. The potting media of the invention are very suitable for the embedding of membranes in selectively acting dialysers and in particular in selectively acting hemodialysers. The potting media of the invention are very advantageously employed for the embedding of membranes in devices used in the detoxification of blood.

The potting media of the present invention can be advantageously employed in in casting processes and in particular in centrifugal casting processes.

The production of the polyurethane embedding media of the present invention corresponds to the processes disclosed in German patent disclosure Nos. 2,813,197; 2,855,243 and 2,907,501 except as otherwise stated herein. In particular the present invention provides for the addition of a catalyst. The catalyst can be added to the starting components employed in the production of the prepolymer that is to the mixture of castor oil and trimethylolpropane or to the diisocyanate. Of course, the catalyst can also be added after the production of the prepolymer is performed. The catalyst can also be added to the castor oil or mixture of castor oil and trimethylolpropane serving as a crosslinking agent.

It was particularly surprising that small amounts of catalyst in accordance with the present invention can effect that both the production as well as the processing of the potting media are influenced advantageously. Thus the processing time is ideally reduced. In addition the course of the viscosity during the embedding is so good that no problems occur. The hardening time is reduced.

It is very advantageous to process the embedding media at temperatures of about 50° C. However, they can also advantageously be employed at lower temperatures such as for example room temperature.

In addition to the improvements relating to the production and to the processability of the potting media, the invention also provides advantages relating to the properties of the potting media such as their mechanical properties. In addition, the hardness values are reached considerably sooner than with polyurethanes without the catalyst addition of the present invention. This means that the castings can be taken after very short times out of the molds.

The inherent color of the embedding media is clear and only weakly tinged yellow. An additional advantage of the potting media of the present invention comprises that they are not or only in a negligible amount attacked by usual liquids contacted during their use and therefor there is no danger that undesired materials are dissolved or pass into the dialyzate or retentate. Therefor, the embedding media of the present invention are excellently suitable as potting media for membranes and in particular for the embedding of membranes into artificial organs. They serve especially for the embedding of membranes such as hollow fibers, hollow threads, tube foils, films or flat foils. Membranes embedded in this manner are advantageously employed in selectively acting dialysers, and especially hemodialysers, as well as in other devices serving for the detoxification of blood.

It is further advantageous that a temperature increase occurs only to a very minor degree even though the hardening times of the method of the present invention are shorter as compared with the method without catalyst and this is particularly advantageous in the embedding of membranes sensitive to temperature.

Based on the excellent viscosity behavior upon embedding the potting media are very well suited for casting processes and in particular for centrifugal casting. The embedding media are distributed very rapidly based on their excellent viscosity behavior around the membranes to be embedded and fill all spaces and do not allow any voids to occur. The wetting of the membranes with the potting medium is excellent. An undesirable, to high rising of the potting medium based on capillary forces at the membranes does not occur. The potting medium does not tend to form bubbles.

The embedding media can be mixed very well at room temperature and can then be crosslinked at elevated temperatures such as for example 50° C.

Based on the favorable course of the viscosity over time of the potting media during crosslinking, the potting media are in particular suited for the automatic embedding of membranes. A mixing in an automatic apparatus is very well possible at temperatures such as for example 50° C. at which the crosslinking is to be performed.

EXAMPLE 1

Production of a Prepolymer without Catalyst

Starting materials:
  84.73 kg 4,4'-diphenylmethane-diisocyanate with 25 weight percent of dimerized and trimerized diisocyanate (Commercial product: Isonate 143 L)
  17.06 kg Castor oil, German medicines book DAB 8
  3.205 kg Trimethylolpropane The liquid diisocyanate is filled in a reactor and warmed under stirring and purging with nitrogen to 65° C.

In a second reactor castor oil and trimethylolpropane are successively filled under stirring and nitrogen purging and are stirred for about one hour at 85° C. Then the heating is discontinued and care is taken that the temperature does not drop to below 60° C.

The contents of the second reactor is then added in the course of one hour to the liquid diisocyanate preheated to 65° C. under stirring and nitrogen purging. Through cooling the temperature is kept to about 70° C. during the reaction.

After termination of the addition of the mixture of trimethylolpropane and castor oil the total mixture is kept for an additional 2 hours at 70° C. The mixture should then theoretically have a contents of 18.85 weight percent of isocyanate.

The final prepolymer is then cooled to a temperature of 60° C., is degassed by evacuation under slow stirring and emptied into dry, nitrogen purged containers in submerged filling and is thus directly suited for the production of the potting medium by crosslinking.

EXAMPLE 2

Production of the Catalyst Containing Crosslinking Agent

Starting materials:
  75.33 kg Castor Oil, German medicines book DAB 8
  0.67 kg Trimethylolpropane
  4.955 g Dibutyltin-dilaurate The castor oil and the trimethylolpropane are filled into a reactor and are stirred for about an hour at about from 80° to 90° C. internal temperature. In the meantime the catalyst is dissolved in a small residue of the castor oil (0.33 kg) in a beaker with slight heating at temperatures below 50° C. and is then added to the main solution.

After cooling of the clear, well stirrable mixture to temperatures below 50° C., gas is removed by evacuation under slowed down stirring and the mixture is emptied into dry, nitrogen purged vessels in submerged filling.

Thus the crosslinking agent is directly employable for the crosslinking of the prepolymer.

EXAMPLE 3

Embedding of Hollow Fiber Membranes 25.8 g of the prepolymer prepared according to Example 1 and having room temperature are mixed at 25° C. with 43.2 g of the crosslinking agent prepared according to Example 2 being stored at room temperature and the mixture is then evacuated to free it from gases. This step takes about 15 minutes. Then the mixture has a viscosity of about from 8 to 11 Pa.s.

A Cuprophane hollow fiberbundle (Cuprophane is a registered trademark of Enka AG, whereunder in 1980 cellulose hollow fibers were offered, which were produced by the copper oxide-ammonia process) was embedded in a hemodialyser with 60 g of the described mixture in accordance with the centrifugal casting process. The centrifuge is operated at 500 rpm at room temperature. After about 35 minutes the dialyser is removed from the centrifuge and cut for the opening of the hollow fiber ends. The hardened polyurethane can be cut without any difficulties. A smooth cutting face is produced without generation of cutting dust. The adhesion to the Cuprophane hollow fibers is excellent.

EXAMPLE 4

Production of Catalyst Containing Prepolymer

Starting materials:
- 84.73 kg 4,4'-diphenylmethane-diisocyanate (Isonate 143L)
- 17.06 kg Castor Oil German medicines book DAB 8
- 3.205 kg trimethylolpropane
- 11.0 g Di-n-butyltin-dinonanoate The liquid diisocyanate is filled in a reactor and heated under stirring and purging with nitrogen to about 60° C. internal temperature. Then stirring and heating is continued until a completely clear solution is present.

Initially half the amount of castor oil and then the trimethylolpropane amount are filled into a second reactor under stirring and nitrogen purging. At the same time the catalyst is predissolved in about 0.5 kg of castor oil, which is added to the castor oil trimethylolpropane solution and it is afterflushed with the balance amount of the castor oil. The mixture is stirred for about an hour at 85° C. until a clear solution is present. Then the solution is cooled to about 65° C.

The solution of trimethylolpropane, castor oil and tin catalyst is now added over one hour to the diisocyanate heated to 60° C. under stirring and nitrogen purging. By way of cooling the temperature of the reaction is kept to about from 65° to 75° C.

After termination of the adding the mixture is left for another hour at 75° C. under stirring for further reacting. The mixture then has theoretically a contents of 18.85 weight percent of isocyanate, which in practical situations however may be lower with a minimum being about 18.2 weight percent.

The prepolymer produced in this manner is cooled to below 60° C., it is degassed by evacuation under slowed stirring and it is emptied into dry, nitrogen purged containers in submerged filling.

EXAMPLE 5

Production of the Crosslinking Agent without Catalyst

Starting materials:
- 75.33 kg castor oil German medicines book DAB 8
- 0.67 kg trimethylolpropane The castor oil and the trimethylolpropane are successively filled into a reactor and are maintained at 85° C.±5° C. under stirring and nitrogen purging. After cooling of the clear mixture to temperatures below 50° C., the mixture is degassed by evacuation under slowed down stirring and the mixture is emptied into dry, nitrogen purged vessels in submerged filling.

EXAMPLE 6

Automatic Embedding of Hollow Fiber Bundles

The prepolymer and the crosslinking agent are filled into an apparatus for automatic embedding of hollow fiber bundles as described in the prospectus 600 H series Processing Systems for Urethane Elastomers of the Company Fluidyne Instrumentation, 1631 San Pablo Avenue, Oakland, Calif. 94612.

50 g degassed polyurethane mixture, which in each case comprises 21.5 g of the prepolymer heated to 50° C. and 28.5 g of the chain extender also heated to 50° C., are pushed out automatically per time unit for the casting of dialysers.

A removal from the mold is possible after about 20 minutes.

EXAMPLE 7

Production of the Prepolymer

Starting materials:
- 64.63 kg 4.4'-diphenylmethane-diisocyanate (Isonate 143 L)
- 15.22 kg isophorone-diisocyanate
- 16.96 kg castor oil German medicines book DAB 8
- 3.19 kg trimethylolpropane
- 15.0 g di-n-butyltin-dinonanoate The two isocyanates are filled in a reactor and are heated under stirring and nitrogen purging to 80° C. until the contents of the reactor is present as a clear solution.

The further processing is performed in the same way as described under Example 1. The finished mixture has a theoretical contents in isocyanate of 19.67 weight percent, which in practical cases can vary by about 0.4 weight percent.

After termination of the reaction, that is as soon as the finished prepolymer is present, the indicated amount of catalyst is added at 60° C. Previously the catalyst was dissolved in about one kg of the prepolymer and is then fed under stirring to the total amount. The degassing and the emptying is then performed as indicated under Example 1.

EXAMPLE 8

42 parts by weight of the prepolymer according to Example 7 and 58 weight percent of the crosslinking agent according to Example 2 are mixed with each other at room temperature under vigorous stirring within 2 minutes for the embedding of foils. The mixture is then under evacuation degassed for 3 minutes. The embedding is performed as is conventionally known by injection into a correspondingly prepared mold of the reaction mixture and the mold comprises 20 flat foils. The embedding mass is hardened at room temperature. After about 40 minutes it is possible to remove the mold.

The time before removal of the mold can be shortened to about 20 minutes in cases where the mixture is heated to about 50° C. for hardening.

It will be understood that each of the compositions described above, or two or more together, may also find a useful application in other types of systems and fields of plastics applications differing from the types described above.

While the invention has been illustrated and described as embodied in the context of a potting medium, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A potting medium comprising a polymer including groups derived from reacting castor oil, trimethylolpropane and a diisocyanate based on a carbon ring compound; and a dialkyltin compound in a amount of from about 5 to 50 ppm calculated for elementary tin based on the total weight of potting medium.

2. The potting medium according to claim 1 wherein the carbon ring compound comprises up to 30 carbon atoms.

3. The potting medium according to claim 2 wherein the carbon ring compound comprises up to 15 carbon atoms.

4. The potting medium according to claim 1 wherein the diisocyanate based on a carbon ring compound comprises an aromatic diisocyanate.

5. The potting medium according to claim 4 wherein the aromatic diisocyanate includes 4,4'-diphenylmethane-diisocyanate.

6. The potting medium according to claim 1 wherein the diisocyanate based on a carbon ring compound comprises an alicyclic diisocyanate.

7. The potting medium according to claim 6 wherein the alicyclic diisocyanate includes 3-isocyanatomethyl-3,5,5-trimethylol-cyclohexyl-isocyanate.

8. The potting medium according to claim 7 wherein the 3-isocyanatomethyl-3,5,5-trimethylol-cyclohexyl-isocyanate has a content of from about 18 to 28 mole percent of dimeric or trimeric diisocyanate.

9. The potting medium according to claim 7 wherein the percentage of 3-isocyanatomethyl-3,5,5-trimethylol-cyclohexyl-isocyanate relative to the total amount of diisocyanate based on a carbon ring compound is from about 10 to 50 mole percent.

10. The potting medium according to claim 1 wherein the polymer includes groups derived from a prepolymer having NCO-groups and containing groups derived from reacting trimethylolpropane, castor oil and a diisocyanate based on a carbon ring compound.

11. The potting medium according to claim 10 wherein the polymer includes groups derived from the prepolymer as reacted with castor oil.

12. The potting medium according to claim 10 wherein the polymer includes groups derived from the prepolymer as reacted with a mixture of castor oil and trimethylolpropane.

13. The potting medium according to claim 1 wherein the dialkyltin compound comprises up to about 50 carbon atoms.

14. The potting medium according to claim 1 wherein the dialkyltin compound includes dialkyltin-dialkanoate.

15. The potting medium according to claim 14 wherein the dialkyltin-dialkanoate includes dibutyltin-dilaurate.

16. The potting medium according to claim 14 wherein the dialkyltin-dialkanoate includes di-n-butyltin-dinonanoate.

17. The potting medium according to claim 1 wherein the dialkyltin compound includes a dialkyltin-mercaptide.

18. The potting medium according to claim 1 wherein the dialkyltin compound is present in an amount of from about 5 to 15 ppm calculated for elementary tin.

19. A method for production of a potting medium comprising adding to at least one of the ingredients employed a dialkyltin compound in an amount resulting in a content of the potting medium of from about 5 to 50 ppm calculated for elementary tin;

reacting a diisocyanate based on a carbon ring compound in stochiometric excess with a mixture of castor oil and trimethylolpropane to a prepolymer having NCO-groups; and mixing the prepolymer with castor oil for crosslinking.

20. The method for production of a potting medium according to claim 19 further comprising adding trimethylolpropane to the castor oil employed in mixing with the prepolymer.

21. The method for production of a potting medium according to claim 19 further comprising hardening the mixture.

22. The method for production of a potting medium according to claim 19 wherein the dialkyltin is added to the prepolymer composition.

23. The method for production of a potting medium according to claim 19 wherein the dialkyltin compound is added to the castor oil to be mixed with the prepolymer.

24. The method for production of a potting medium according to claim 19 wherein the prepolymer is prepared at a temperature of from about 40° to 100° C.

25. The method for production of a potting medium according to claim 24 wherein the prepolymer is prepared at a temperature of from about 60° to 75° C.

26. The method for production of a potting medium according to claim 19 wherein the carbon ring compound comprises up to 30 carbon atoms.

27. The method for production of a potting medium according to claim 26 wherein the carbon ring compound comprises up to 15 carbon atoms.

28. The method for production of a potting medium according to claim 19 wherein the diisocyanate based on a carbon ring compound comprises an aromatic diisocyanate.

29. The method for production of a potting medium according to claim 28 wherein the aromatic diisocyanate includes 4,4'-diphenylmethane-diisocyanate.

30. The method for production of a potting medium according to claim 19 wherein the diisocyanate based on a carbon ring compound comprises an alicyclic diisocyanate.

31. The method for production of a potting medium according to claim 30 wherein the alicyclic diisocyanate includes 3-isocyanatomethyl-3,5,5-trimethylol-cyclohexyl-isocyanate.

32. The method for production of a potting medium according to claim 31 wherein the 3-isocyanatomethyl-3,5,5-trimethylol-cyclohexyl-isocyanate has a content of from about 18 to 28 mole percent of dimerized or trimerized diisocyanate.

33. The method for production of a potting medium according to claim 31 wherein the percentage of 3-isocyanatomethyl-3,5,5-trimethylol-cyclohexyl-isocyanate relative to the total amount of diisocyanate based on a carbon ring compound is from about 10 to 50 mole percent.

34. The method for production of a potting medium according to claim 19 wherein the dialkyltin compound comprises up to about 50 carbon atoms.

35. The method for production of a potting medium according to claim 19 wherein the dialkyltin compound includes dialkyltin-dialkanoate.

36. The method for production of a potting medium according to claim 35 wherein the dialkyltin-dialkanoate includes dibutyltin-dilaurate.

37. The method for production of a potting medium according to claim 35 wherein the dialkyltin-dialkanoate includes di-n-butyltin-dinonanoate.

38. The method for production of a potting medium according to claim 19 wherein the dialkyltin compound includes a dialkyltin-mercaptide.

39. The method for production of a potting medium according to claim 19 wherein the dialkyltin compound is present in an amount of from about 5 to 15 ppm calculated for elementary tin.

* * * * *